United States Patent [19]

Ostersehlt et al.

[11] Patent Number: 4,851,410
[45] Date of Patent: Jul. 25, 1989

[54] 1,4-DISUBSTITUTED PYRAZOLE DERIVATIVES, COMPOSITIONS AND USE

[75] Inventors: Bernd Ostersehlt, Maxdorf; Norbert Rieber, Mannheim; Josef Gries, Wachenheim, all of Fed. Rep. of Germany

[73] Assignee: BASF Aktiengesellschaft, Ludwigshafen, Fed. Rep. of Germany

[21] Appl. No.: 273,178

[22] Filed: Nov. 15, 1988

Related U.S. Application Data

[63] Continuation of Ser. No. 901,579, Aug. 29, 1986, abandoned.

[30] Foreign Application Priority Data

Sep. 29, 1986 [DE] Fed. Rep. of Germany ....... 3532880

[51] Int. Cl.[4] ................. A61K 31/425; A61K 31/535; C07D 417/12; C07D 417/14
[52] U.S. Cl. ............................ 514/232.2; 514/236.2; 514/316; 514/326; 514/362; 544/82; 544/134; 546/187; 546/211; 548/135
[58] Field of Search ................. 544/82, 134; 546/187, 546/211; 548/135; 514/232.2, 236.2, 316, 326, 362

[56] References Cited

U.S. PATENT DOCUMENTS

| | | | |
|---|---|---|---|
| 4,330,544 | 5/1982 | Jarreau et al. | 548/376 |
| 4,374,248 | 2/1983 | Crenshaw et al. | 548/127 |
| 4,447,441 | 5/1984 | Yellin et al. | 514/407 |
| 4,464,374 | 8/1984 | Yellin et al. | 514/407 |
| 4,639,519 | 1/1987 | Ganellin et al. | 544/320 |
| 4,659,721 | 4/1987 | Schickaneder et al. | 548/214 |

FOREIGN PATENT DOCUMENTS

| | | | |
|---|---|---|---|
| 1201436 | 3/1986 | Canada | 548/214 |
| 0004793 | 10/1979 | European Pat. Off. | 544/320 |
| 0117345 | 9/1984 | European Pat. Off. | 544/320 |

OTHER PUBLICATIONS

Chem. Abst. vol. 99, No. 1, pp. 1 and 185, col. 2, No. 1737b (1983).

*Primary Examiner*—Robert W. Ramsuer
*Attorney, Agent, or Firm*—Keil & Weinkauf

[57] ABSTRACT

1,4-disubstituted pyrazole derivatives of the formula I

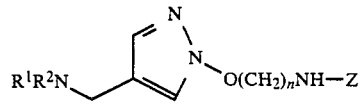

where $R^1$ and $R^2$ independently of one another are each hydrogen, lower alkyl or benzyl, or $R^1$ and $R^2$, together with the nitrogen atom to which they are bonded, may be a pyrrolidino, piperidino or morpholino radical, n is an integer from 2 to 5 and Z is a radical of the formula

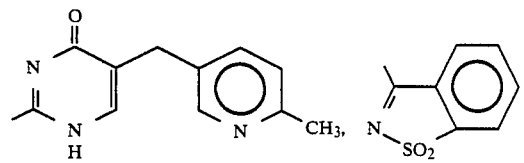

or $QNR^1R^2$ where $R^1$ and $R^2$ have the same meanings as above, Q is

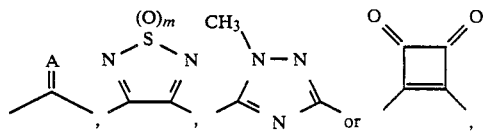

A is $CHR^3$ or $NR^3$ in which $R^3$ is CN, $NO_2$, $SO_2$-aryl or $SO_2$-lower alkyl and m may be 0 or 1, and their pharmaceutically tolerated salts, processes for their preparation, pharmaceutical compositions containing the compounds of formula I, the use of such compositions and an intermediate of the formula III

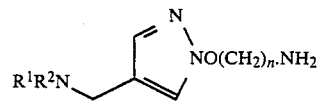

where $R^1$, $R^2$ and n have the same meanings as above, in the preparation of the compounds of the formula I.

The compounds are useful to block histamine $H_2^-$ receptors.

7 Claims, No Drawings

1,4-DISUBSTITUTED PYRAZOLE DERIVATIVES, COMPOSITIONS AND USE

This application is a continuation of application Ser. No. 901,579, filed on Aug. 29, 1986, abandoned.

The present invention relates to novel 1,4-disubstituted pyrazole derivatives having a selective action on histamine $H_2$ receptors.

The division of the histamine receptors into two groups, ie. $H_1$ and $H_2$ receptors, has been proposed by Ash and Schild (Brit. J. Pharmacol. Chemother., 27 (1966), 427) and by Black et al. (Nature, 236 (1972), 385). Compounds which act as histamine $H_2$ receptor blockers are useful for the treatment of disorders associated with a pathologically increased secretion of gastric acid, eg. gastric and duodenal ulcers. Examples of such compounds which are already used therapeutically are cimetidine (U.S. Pat. No. 3,950,333) and ranitidine (U.S. Pat. No. 4,128,658). However, their activity is relatively weak, so that large dosage units have to be administered daily. There is therefore a need for novel, selective antagonists to histamine $H_2$ receptors which have improved activity. Compounds of this type are provided by the invention.

The present invention relates to 1,4-disubstituted pyrazole derivatives of the general formula I where $R^1$ and $R^2$ independently of one another are each hydrogen, lower alkyl or benzyl, or $R^1$ and $R^2$, together with the nitrogen atom to which they are bonded, may be a pyrrolidino, piperidino or morpholino radical, n is an integer from 2 to 5, and Z is a radical of the formula or $QNR^1R^2$ where $R^1$ and $R^2$ have the same meanings as above, Q is A is $CHR^3$ or $NR^3$ in which $R^3$ is CN, $NO_2$, $SO_2$-aryl or $SO_2$-lower alkyl, an m may be 0 or 1, and their pharmaceutically tolerated salts.

In a preferred group of compounds, n is 4.

In another preferred group of compounds, Z is where $R^1$ is hydrogen and $R^2$ is hydrogen or lower alkyl.

Lower alkyl is always understood as being $C_1$-$C_4$-alkyl.

Examples of novel compounds of the formula I are:
N-methyl-N'-[3-(4-piperidinomethylpyrazol-1-yloxy)-propylamino]-cyanoguanidine,
N-methyl-N'-[3-(4-dimethylaminomethylpyrazol-1-yloxy)-propylamino]-cyanoguanidine,
N-methyl-N'-[4-(4-piperidinomethylpyrazol-1-yloxy)-butylamino]-cyanoguanidine,
N-methyl-N'-[4-(4-dimethylaminomethylpyrazol-1-yloxy)-butylamino]-cyanoguanidine,
1-methylamino-1-[3-(4-N,N-dimethylaminomethylpyrazol-1-yloxy)-propylamino]-2-nitroethylene,
1-methylamino-1-[3-(4-piperidinomethylpyrazol-1-yloxy)-propylamino]-2-nitroethylene,
1-methylamino-1-[4-(4-N,N-dimethylaminomethylpyrazol-1-yloxy)-butylamino]-2-nitroethylene,
1-methylamino-1-[4-(4-piperidinomethylpyrazol-1-yloxy)-butylamino]-2-nitroethylene,
2-[3-(4-piperidinomethylpyrazol-1-yloxy)-propylamino]-5-(2-methyl-5-pyridylmethyl)-pyrimid-4-one,
2-[4-(4-piperidinomethylpyrazol-1-yloxy)-butylamino]-5-(2-methyl-5-pyridylmethyl)-pyrimid-4-one,
3-amino-4-[3-(4-piperidinomethylpyrazol-1-yloxy)-propylamino]-cyclobutene-1,2-dione,
3-amino-4-[4-(4-piperidinomethylpyrazol-1-yloxy)-butylamino]-cyclobutene-1,2-dione,
3-methylamino-4-[3-(4-piperidinomethylpyrazol-1-yloxy)-propylamino]-cyclobutene-1,2-dione,
3-methylamino-4-[4-(4-piperidinomethylpyrazol-1-yloxy)-butylamino]-cyclobutene-1,2-dione,
1-methyl-3-amino-4-[3-(4-piperidinomethylpyrazol-1-yloxy)-propylamino]-1,2,4-triazole,
1-methyl-3-amino-4-[4-(4-piperidinomethylpyrazol-1-yloxy)-butylamino]-1,2,4-triazole,
1-methyl-3-amino-4-[5-(4-piperidinomethylpyrazol-1-yloxy)-pentylamino]-1,2,4-triazole,
1-methyl-3-amino-4-[3-(4-dimethylaminomethylpyrazol-1-yloxy)-propylamino]-1,2,4-triazole,
1-methyl-3-amino-4-[4-(4-dimethylaminomethylpyrazol-1-yloxy)-butylamino]-1,2,4-triazole,
4-methylamino-3-[3-(4-piperidinomethylpyrazol-1-yloxy)-propylamino]-1,2,4-thiadiazole 1-oxide,
4-methylamino-3-[4-(4-piperidinomethylpyrazol-1-yloxy)-butylamino]-1,2,5-thiadiazole 1-oxide,
4-methylamino-3-[3-(4-dimethylaminomethylpyrazol-1-yloxy)-propylamino]-1,2,5-thiadiazole 1-oxide,
4-methylamino-3-[4-(4-dimethylaminomethylpyrazol-1-yloxy)-butylamino]-1,2,5-thiadiazole 1-oxide,
4-amino-3-[3-(4-dimethylaminomethylpyrazol-1-yloxy)-propylamino]-1,2,5-thiadiazole 1-oxide,
4-amino-3-[4-(4-dimethylaminomethylpyrazol-1-yloxy)-butylamino]-1,2,5-thiadiazole 1-oxide,
4-amino-3-[3-(4-piperidinomethylpyrazol-1-yloxy)-propylamino]-1,2,5-thiadiazole 1-oxide,
4-amino-3-[4-(4-piperidinomethylpyrazol-1-yloxy)-butylamino]-1,2,5-thiadiazole 1-oxide, 4-amino-3-[5-(4-piperidinomethylpyrazol-1-yloxy)-pentylamino]-1,2,5-thiadiazole 1-oxide,
4-amino-3-[4-(4-di-n-butylaminomethylpyrazol-1-yloxy)-butylamino]-1,2,5-thiadiazole 1-oxide,
4-amino-3-[4-(4-pyrrolidinomethylpyrazol-1-yloxy)-butylamino]-1,2,5-thiadiazole 1-oxide,
4-amino-3-[4-(4-morpholinomethylpyrazol-1-yloxy)-butylamino]-1,2,5-thiadiazole 1-oxide,
4-amino-3-[4-(4-N-methyl-N-benzylaminomethyl-pyrazol-1-yloxy)-butylamino]-1,2,5-thiadiazole 1-oxide,
3-[4-(4-dimethylaminomethylpyrazol-1-yloxy)-butylamino]-benzoisothiazole 1,1-dioxide,
3-[4-(4-piperidinomethylpyrazol-1-yloxy)-butylamino]-benzoisothiazole 1,1-dioxide,
4-amino-3-[4-(4-dimethylaminomethylpyrazol-1-yloxy)-butylamino]-1,2,5-thiadiazole,
4-amino-3-[4-(4-piperidinomethylpyrazol-1-yloxy)-butylamino]-1,2,5-thiadiazole.

Examples of suitable physiologically tolerated organic or inorganic acids for forming salts are hydrochloric acid, hydrobromic acid, phosphoric acid, sulfuric acid, maleic acid, fumaric acid, lactic acid, tartaric acid, malic acid, citric acid, salicylic acid, adipic acid and benzoic acid. Other acids are given in Fortschritte der Arzneimittelforschung, 10 (1966), 224–225, Birkhauser-Verlag, Basel and Stuttgart.

The present invention furthermore relates to processes for the preparation of compounds of the formula I wherein, (a) for the preparation of compounds of the formula I where Z is

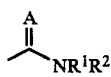

a thio compound of the formula II

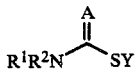   II where $R^1$, $R^2$ and A have the same meanings as above and Y is lower alkyl, is reacted with an amine of the formula III

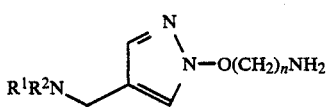   III where $R^1$, $R^2$ and n have the stated meanings, or a compound of the formula III is reacted with a compound of the formula IV or V

   IV

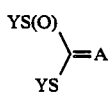   V where A and Y have the same meanings as above, and the resulting compound of the formula VI

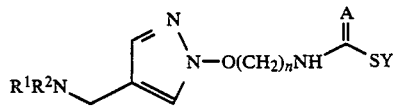   VI where $R^1$, $R^2$, n and A have the stated meanings, is reacted with an amino compound of the formula VII

HNR$^1$R$^2$   VII where $R^1$ and $R^2$ have the same meanings as above, or (b) for the preparation of compounds of the formula I where Z is

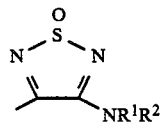

a thiadiazole derivative of the formula VIII

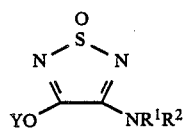   VIII where $R^1$, $R^2$ and Y have the same meanings as above, is reacted with a compound of the formula III, or a compound of the formula III is reacted with a compound of the formula IX

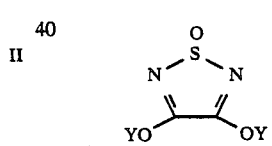   IX where Y is lower alkyl, and the resulting compound of the formula X

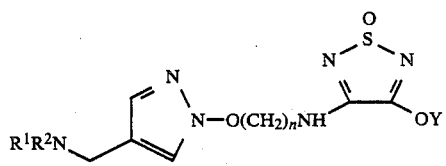   X is reacted with an amino compound of the formula VII, or (c) for the preparation of compounds in which Z is

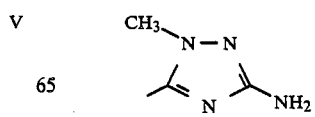

a hydrazine derivative of the formula XI

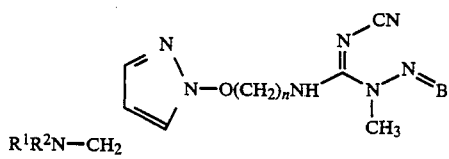 XI

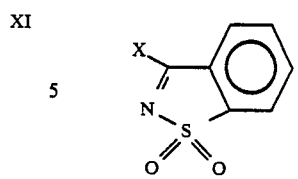 XV where Y is lower alkyl and B is a protective group, eg. =CH—φ, is reacted with a compound of the formula III, and the reaction product is catalytically cleaved in the presence of an acid and subjected to cyclization, or (d) for the preparation of compound of the formula I where Z is

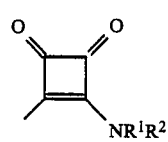

a quadratic acid derivative of the formula XII

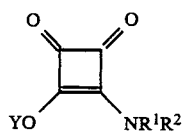 XII where $R^1$, $R^2$ and Y have the same meanings as above, is reacted with a compound of the formula III, or a quadratic acid derivative of the formula XIII

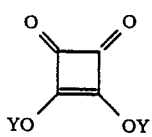 XIII where Y is (lower) alkyl, is reacted with a compound of the formula III and the resulting product of the formula XIV

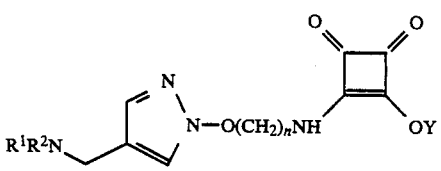 XIV where $R^1$, $R^2$, Y and n have the same meanings as above, is reacted with an amine of the formula VII, or (e) for the preparation of compounds of the formula I where Z is

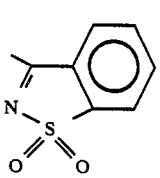

a compound of the formula XV where X is a suitable leaving group, such as halogen, OY or SY, where Y is lower alkyl, is reacted with a compound of the formula III, or (f) for the preparation of compounds of the formula I where Z is

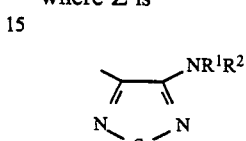

a compound of the formula I, where Z is

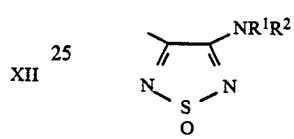

is treated with a strong acid and the product of the formula XVI

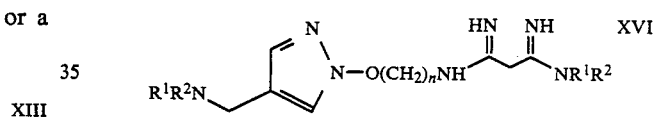 XVI is reacted with a compound of the formula XVII

L—S—L    XVII where L is a suitable leaving group, preferably phthalimido, and the resulting compound is converted to its salts with physiologically tolerated acids, or (g) for the preparation of compounds of the formula I where Z is

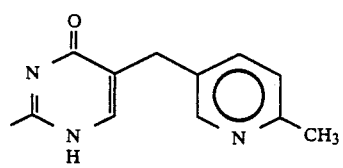

a compound of the formula III is reacted with a compound of the formula

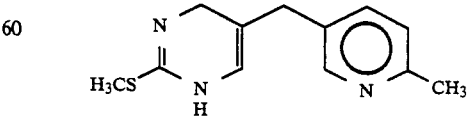

Reaction (a) is carried out at from room temperature to 140° C., advantageously from 50° to 120° C., under atmospheric pressure or in a closed vessel under superatmospheric pressure, if necessary with heating to the stated temperature. It takes place particularly smoothly when Y is methyl.

The starting compounds can be reacted directly, ie. without the addition of a diluent. Advantageously, however, the reaction is carried out in the presence of an inert diluent or solvent, for example a lower alcohol of 1 to 4 carbon atoms, such as methanol, ethanol or propanol, a lower saturated dialkyl ether, dialkyl glycol ether or cyclic ether, such as diethyl ether, 1,2-dimethoxy ether, tetrahydrofuran or dioxane, a dialkylformamide, such as dimethylformamide or diethylformamide, dimethyl sulfoxide, acetonitrile or water, or in a mixture of the stated solvents. Lower alcohols, preferably methanol and ethanol, and water are the most suitable.

The completeness of the reaction depends on the reaction temperature, the reaction generally being complete in from 2 to 25 hours. The product can then be isolated in a conventional manner, for example by filtration or by distilling off the diluent or solvent from the reaction mixture. The resulting compounds are purified in a conventional manner, for example by recrystallization from a solvent, conversion to the salt of a physiologically tolerated acid, or column chromatography.

Reactions (b)–(e) and (g) are carried out in the presence of a solvent, for example a lower alcohol of 1 to 4 carbon atoms, preferably methanol, ethanol or isopropanol, a lower saturated dialkyl ether or cyclic ether, such as diethyl ether, methyl tert-butyl ether or tetrahydrofuran, a lower chlorohydrocarbon, such as methylene chloride or chloroform, a dialkylformamide, such as dimethylformamide or diethylformamide, dimethyl sulfoxide or water. An inorganic or organic base, for example an alkali metal or alkaline earth metal carbonate or a tertiary amine, such as triethylamine or pyridine, can, if necessary, be added to the reaction mixture. The reaction is effected at from 0° to 100° C. under atmospheric pressure. The reaction products can be isolated in the manner described for (a). Process (f) is known and is described in principle in, for example, German Laid-Open Application No. DOS 3,211,281.

For the processes for the preparation of the novel compounds, primary amines of the formula III are used. These amines are novel compounds. The invention also embraces these compounds and their addition salts with acids. The amines of the formula III can be prepared by a method in which (h) 1-hydroxypyrazole is reacted with a phthalimido compound of the formula XVIII

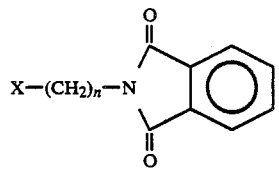
XVIII where n has the same meanings as above and X is a leaving group, eg. halogen or sulfonyloxy, such as mesyl or tosyl, using a base, such as an alkali metal carbonate, hydroxide or alkoxide, or sodium hydride, in an inert solvent, such as toluene, xylene, tetrahydrofuran or dimethylformamide.

The reaction product of the formula XIX

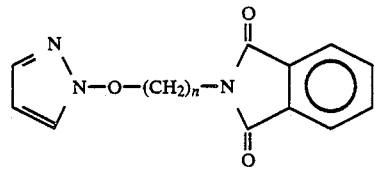
XIX is then subjected to a Mannich reaction, preferably with a reagent of the formula XX

XX where $R^1$ and $R^2$ have the same meanings as above. The reaction is carried out in an inert solvent, preferably acetonitrile or dimethylformamide, at elevated temperature, preferably at from 50° to 150° C.

Finally, the phthalimido protective group in the resulting compound of the formula XXI

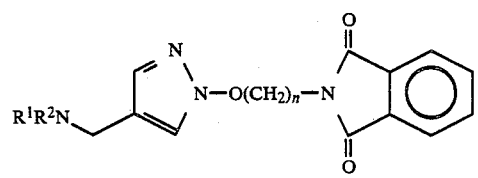
XXI can be eliminated by means of a suitable reagent, such as an alkali metal hydroxide or a primary amine, such as methylamine or ethanolamine, or hydrazine. The amines of the formula III may also be prepared by a method in which (i) methyl 1-hydroxypyrazole-4-carboxylate is reacted with an ω-substituted aldehyde-acetal of the formula XXII

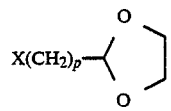
XXII where X has the same meanings as above and p is n−1. The process is similar to that described for the reaction of XVIII. In the reaction product of the formula XXIII, the ester group is hydrolyzed to the carboxylic acid and then converted to the amide with an amine of the formula VII. To do this, carboxylic acid is converted temporarily to an activated derivative, for example an acyl halide, an hydride or an activated ester.

The intermediate of the formula XXIV is converted with a dilute aqueous mineral acid in a conventional manner to the aldehyde XXV, and the latter is reacted with hydroxylamine to give the oxime XXVI.

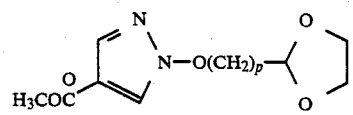
XXIII

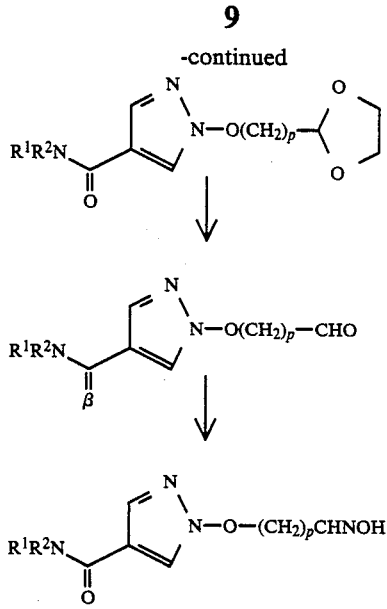

The oxime XXVI can be converted to the amine III with suitable reducing agents, for example complex metal hydrides, such as lithium aluminum hydride.

The starting substances of the formulae II, IV, V, VIII, IX, XI, XII, XIII, XV, XVII, XVIII, XX and XXII are known from the literature or can be prepared by a known method.

Finally, the present invention relates to drugs which contain, in addition to conventional carriers and diluents, a compound of the formula I or its physiologically tolerated salt as an active compound.

The novel compounds and their physiologically tolerated addition salts with acids possess useful pharmacological properties. They are histamine antagonists with a powerful and specific action on histamine $H_2$ receptors and are therefore particularly useful for the pharmacotherapeutic treatment of disorders associated with a pathologically increased secretion of gastric acid, for example gastric or duodenal ulcers.

The compounds according to the invention can be administered in a conventional manner, either orally or intravenously. The dosage depends on the age, condition and weight of the patient and on the route of administration. As a rule, the daily dose of active compound is from about 0.1 to 20 mg/kg of body weight for oral administration and from 0.01 to 10 mg/kg of body weight for intravenous administration. In particular cases, however, it may be necessary to increase the doses.

The novel compounds may be employed in the conventional solid or liquid pharmaceutical forms, such as tablets, capsules, powders, granules, coated tablets or solutions. These are prepared in a conventional manner and to do so the active compounds can be mixed with the conventional pharmaceutical auxiliaries, such as talc, gum arabic, sucrose, lactose, cereal starch or cornstarch, potato flour, magnesium stearate, alginates, gum tragacanth, carraghenates, polyvinyl alcohol, polyvinylpyrrolidone, aqueous or nonaqueous carriers, wetting agents, dispersants, emulsifiers and/or preservatives (cf. Hagers Handbuch der Pharmazeut. Praxis, 4th edition, Springer-Verlag, Berlin, Heidelberg, New York 1967–1980, vol. VII A and B). The formulations thus obtained customarily contain from 0.1 to 99 percent by weight of the active compound.

The Examples which follow illustrate the invention (the NMR data are stated in the form of δ values (ppm)).

A. Preparation of the starting compounds and intermediates

EXAMPLE A

Methyl 1-hydroxypyrazole-4-carboxylate 90 g of 1-hydroxypyrazole-4-carboxylic acid (for preparation, see corresponding German Patent Application No. P 35 32 879.7) are suspended in 500 ml of methanol, and 10 ml of concentrated sulfuric acid are added. The mixture is then refluxed for 12 hours, the methanol is distilled off under reduced pressure, the solid residue is stirred in 400 ml of water, the solution is brought to pH 3 with sodium hydroxide solution, and the product is filtered off under suction and washed with water. The mother liquor is evaporated down, and a further crystalline fraction is obtained. The combined products are dried under reduced pressure to give 91 g (91% of theory) of methyl 1-hydroxypyrazole-4-carboxylate of melting point 175°–181° C. NMR (DMSO-$D_6$): 8.35 s [1]; 7.82 s [1]; 3.80 s [3].

EXAMPLE B (a) Methyl 1-[3-(2-dioxolanyl)-propoxy]-pyrazole-4-carboxylate 21.8 g of sodium hydride (80 percent strength suspension in mineral oil) is introduced into 1.5 l of dry dimethylformamide, and 90 g of methyl 1-hydroxypyrazole-4-carboxylate are added a little at a time to the stirred mixture. When the evolution of hydrogen is complete, stirring is continued for 30 minutes, after which 95.5 g of 2-(3-chloropropyl)-1,3-dioxolane are added dropwise and the mixture is kept at 120° C. for 10 hours. Thereafter, the dimethylformamide is distilled off under reduced pressure, the residue is taken up in methyl tertbutyl ether, and the solution is washed with water, boiled and evaporated down to give 151 g of a slightly colored oil which crystallizes completely. M.p. 40°–42° C. NMR (CDCl$_3$): 7.82 s [1]; 7.70 s [1]; 4.50 t [1]; 4.39 t [2]; 3.85–3.95 m [4]; 3.80 s [3]; 1.75–1.95 m [4].

(b) 1-[3-(2-Dioxolanyl)-propoxy]-pyrazole-4-carboxylic acid 151 g of the above product from (a) are stirred with 650 ml of 2N sodium hydroxide solution at 90° C. until a clear solution has formed. The solution is cooled and then washed with 200 ml of methylene chloride, the aqueous phase is acidified with concentrated hydrochloric acid and extracted several times with methylene chloride, and the extract is dried and evaporated down to give a colorless residue which crystallizes spontaneously. Yield: 129 g (88% of theory, based on methyl 1-hydroxypyrazole-4-carboxylate). M.p.: 85° C.

NMR (CDCl$_3$): 7.92 s [1]; 7.75 s [1]; 4.52 t [2]; 4.35 t [2]; 3.80–4.05 m [4]; 1.75–2.00 m [4].

EXAMPLE C

1-[3-(2-dioxolanyl)-propoxy]-4-(N-piperidylcarbonyl)-pyrazole 14.5 g of pivaloyl chloride are dissolved in 300 ml of methylene chloride. A solution of 12.2 g of triethylamine and 29 g of 1-[3-(2-dioxolanyl)-propoxy]-pyrazole-4-carboxylic acid in 100 ml of methylene chloride is added dropwise at −30° C. When the addition is complete, the mixture is heated to 20° C. and 11.2 g of piperidine are added. The mixture is worked up by washing it with dilute hydrochloric acid and dilute sodium hydroxide solution and evaporating it down. 35 g of slightly colored oil remain.

NMR (CDCl$_3$): 7.60 s [1]; 7.38 s [1]; 4.50 t [1]; 4.35 t [2]; 3.80–4.50 m [4]; 3.50–3.70 m [4]; 1.45–1.95 m [10].

The following are prepared in a similar manner:

(b) 1-[3-(2-Dioxolanyl)-propoxy]-4-(N-pyrrolidinylcarbonyl)-pyrazole

NMR (CDCl$_3$): 7.69 s [1]; 7.48 s [1]; 4.82 t [1]; 4.30 t [2]; 3.75–3.95 m [4]; 3.45–3.70 m [4]; 1.70–2.10 m [8].

(c) 1-[3-(2-Dioxolanyl)-propoxy]-4-(N-morpholinylcarbonyl)-pyrazole

NMR (CDCl$_3$): 7.61 s [1]; 7.36 s [1]; 4.86 t [1]; 4.33 t [2]; 3.80–4.00 m [4]; 3.68 s [8]; 1.75–1.95 m [4].

(d) 1-[3-(2-Dioxolanyl)-propoxy]-pyrazole-4-carboxylic acid N,N-di-n-butylamide

NMR (CDCl$_3$): 7.54 s [1]; 7.30 s [1]; 4.82 t [1]; 4.30 t [2]; 3.70–3.95 m [4]; 3.38 t [4]; 1.75–1.90 m [4]; 1.20–1.70 m [8]; 0.90 t [6].

(e) 1-[2-(2-Dioxolanyl)-propoxy]-pyrazole-4-carboxylic acid N-methyl-N-benzylamide NMR (CDCl$_3$): 7.61 s [1]; 7.40 s [1]; 7.15–7.30 m [5]; 4.83 t [1]; 4.63 s [2]; 4.31 t [2]; 3.75–3.95 m [4]; 3.25 s [3]; 1.80–1.95 m [4].

EXAMPLE D 1-(4-Oxobutoxy)-4-(N-piperidinylcarbonyl)-pyrazole (a)

40 g of 1-[3-(2-dioxolanyl)-propoxy]-4-(N-piperidinylcarbonyl)-pyrazole in a mixture of 150 ml of tetrahydrofuran, 200 ml of water and 4 ml of concentrated sulfuric acid are refluxed for 8 hours. The mixture is cooled and then saturated with sodium chloride, the phases are separated and the aqueous phase is extracted again with tetrahydrofuran. The combined organic phases are evaporated down, the residue is taken up with methylene chloride, the solution is washed with water and the solvent is evaporated off to give 33 g of the title compound in the form of a viscous oil.

NMR: 9.83 s [1]; 7.67 s [1]; 7.43 s [1]; 4.38 t [2]; 3.50–3.80 m [4]; 2.71 t [2]; 1.50–2.30 m [8].

The following are prepared in a similar manner:

(b) 1-(4-Oxobutoxy)-4-(N-pyrrolidinylcarbonyl)-pyrazole

NMR (CDCl$_3$): 9.85 s [1]; 7.85 s [1], 7.65 s [1]; 4.40 t [2]; 3.50–3.80 m [4]; 2.75 t [2]; 1.70–2.30 m [6].

(c) 1-(4-Oxobutoxy)-4-(N-morpholinylcarbonyl)-pyrazole

NMR (CDCl$_3$): 9.81 s [1]; 7.78 s [1]; 7.49 s [1]; 4.40 t [2]; 3.60–3.90 m [8]; 2.75 t [2]; 1.90–2.30 m [2].

(d) 1-(4-Oxobutoxy)-pyrazole-4-carboxylic acid N,N-di-n-butylamide

NMR (CDCl$_3$): 9.75 s [1]; 7.68 s [1]; 7.39 s [1]; 4.30 t [2]; 3.40 t [4]; 2.65 t [2]; 1.20–2.20 m [10]; 0.90 t [6].

(e) 1-(4-Oxobutoxy)-pyrazole-4-carboxylic acid N-methyl-N-benzylamide

NMR (CDCl$_3$): 9.81 s [1]; 7.75 s [1]; 7.52 s [1]; 7.30–7.40 m [5]; 4.77 s [2]; 4.42 t [2]; 3.15 s [3]; 2.75 t [2]; 1.85–2.30 m [2].

EXAMPLE E 4-(4-Piperidinomethylpyrazol-1-yloxy)-butylamine (a)

26 g of 1-(1-(4-oxobutoxy)-4-(N-piperidinylcarbonyl)pyrazole, 9 ml of pyridine and 7.3 g of hydroxylammonium chloride are dissolved in 250 ml of ethanol, and the solution is left to stand for 5 hours at 25° C. Thereafter, the solvent is evaporated off, the residue is taken up in methylene chloride, the solution is washed with dilute hydrochloric acid and water and the resulting clear solution is evaporated down to give 27 g of a viscous oil, which is dissolved in 40 ml of dry tetrahydrofuran. This solution is added dropwise to a suspension of 12 g of lithium aluminum hydride in 350 ml of dry tetrahydrofuran. The mixture is refluxed for 2 hours, cooled and then hydrolyzed, the aluminum hydroxide is filtered off under suction and the filtrate is evaporated down. The residue is taken up with dilute hydrochloric acid, the acidic aqueous solution is washed with methylene chloride, rendered alkaline and extracted again with methylene chloride, and the solvent is distilled off to give 12 g of a slightly colored oil.

NMR (CDCl$_3$): 7.35 s [1]; 7.22 s [1]; 4.35 t [2]; 3.40 s [2]; 2.75 t [2]; 2.30–2.55 m [4]; 1.40–1.85 m [10].

The following are prepared in a similar manner:

(b) 4-(4-Pyrrolidinomethylpyrazol-1-yloxy)-butylamine

NMR (CDCl$_3$): 7.30 s [1]; 7.16 s [1]; 4.30 t [2]; 3.50 s [2]; 2.75 t [2]; 2.40–2.65 m [4]; 1.60–2.00 m [8].

(c) 4-(4-Morpholinomethylpyrazol-1-yloxy)-butylamine

NMR (CDCl$_3$): 7.35 s [1]; 7.23 s [1]; 4.35 t [2]; 3.60–3.83 m [4]; 3.40 s [2]; 3.79 t [2]; 2.35–2.55 m [4]; 1.60–1.80 m [4].

(d) 4-[4-(N-methyl-N-benzylaminomethyl)-pyrazol-1-yloxy]-butylamine

NMR (CDCl$_3$): 7.32 s [6]; 7.22 s [1]; 4.32 t [2]; 3.51 s [2]; 3.45 s [2]; 2.76 t [2]; 2.20 s [3]; 1.50–1.85 m [4].

(e) 4-[4-(N,N-Di-n-butylaminomethyl)-pyrazol-1-yloxy]-butylamine

NMR (CDCl$_3$): 7.25 s [1]; 7.13 s [1]; 4.31 t [2]; 3.48 s [2]; 2.65–2.95 m [2]; 2.20–2.50 m [4]; 1.20–1.80 m [12]; 0.90 t [6].

EXAMPLE F (a) 3-(Pyrazol-1-yloxy)-propylphthalimide 26 g of 1-hydroxypyrazole are added to a suspension of 10 g of sodium hydride (80 percent strength in oil) in 500 ml of xylene. The mixture is stirred for 1 hour, after which 84 g of 3-bromopropylphthalimide are added and the mixture is refluxed for 2 hours. After cooling, the mixture is filtered, the filtrate is evaporated down, the crystalline residue is suspended in diethyl ether and the product is filtered off under suction. 85 g of the title compound of melting point 116°–118° C. are obtained.

NMR (CDCl₃): 7.65–7.85 m [4]; 7.45 d [1]; 7.20 d [1]; 6.15 t [1]; 4.38 t [2]; 3.90 t [2]; 1.90–2.40 m [2].

The following are obtained in a similar manner: 4-(Pyrazol-1-yloxy)-butylphthalimide NMR (CDCl₃): 7.55–7.90 m [4]; 7.30 d [1]; 7.18 d [1]; 6.10 t [1]; 4.35 t [2]; 3.75 t [2]; 1.60–2.00 m [4].

(c) 5-(Pyrazol-1-yloxy)-pentylphthalimide

NMR (CDCl₃): 7.55–7.90 m [4]; 7.30 d [1]; 7.20 d [1]; 6.10 t [1]; 4.25 t [2]; 3.65 t [2]; 1.50–1.90 m [6].

EXAMPLE G (a) 3-(4-N,N-Dimethylaminomethylpyrazol-1-yloxy)-propylphthalimide 8.5 g of 3-pyrazol-1-yloxypropylphthalimide and 5 g of N,N-dimethylmethyleneammonium chloride in 150 ml of acetonitrile are refluxed for 70 hours. Thereafter, the mixture is evaporated down, the residue is taken up in water and the solution is washed with methylene chloride. The aqueous phase is rendered alkaline and extracted with methylene chloride. The solvent is stripped off to give 68 g of the title compound.

NMR (CDCl₃): 7.60–7.80 m [4]; 7.30 s [1]; 7.08 s [1]; 4.30 t [2]; 3.85 t [2]; 3.27 s [2]; 2.20 s [3]; 2.00–2.20 m [2].

The following are prepared in a similar manner:

(b) 3-(4-Piperidinomethylpyrazol-1-yloxy)-propylphthalimide

NMR (CDCl₃): 7.62–7.78 m [4]; 7.81 s [1]; 7.10 s [1]; 4.32 t [2]; 3.84 t [2]; 3.30 s [2]; 2.21–2.48 m [4]; 2.00–2.20 m [2]; 1.35–1.70 m [6].

(c) 4-(4-Piperidinomethylpyrazol-1-yloxy)-butylphthalimide

NMR (CDCl₃): 7.60–7.95 m [4]; 7.26 s [1]; 7.11 s [1]; 4.30 t [2]; 3.71 t [2]; 3.30 s [2]; 2.20–2.50 m [4]; 1.35–2.00 m [10].

(d) 5-(4-Piperidinomethylpyrazol-1-yloxy)-pentylphthalimide

NMR (CDCl₃): 7.55–7.90 m [4]; 7.22 s [1]; 7.10 [1]; 4.25 t [2]; 3.68 t [2]; 3.31 s [2]; 2.20–2.50 m [4]; 1.30–1.90 m [12].

EXAMPLE H (a) 3-(4-N,N-Dimethylaminomethylpyrazol-1-yloxy)-propylamine 6.8 g of 3-(4-N,N-dimethylaminomethylpyrazol-1-yloxy)-propylphthalimide are dissolved in 40 ml of ethanol, 1.2 g of hydrazine hydrate are added and the mixture is refluxed for 5 hours. After cooling, the mixture is acidified with concentrated hydrochloric acid, boiled for a short time, cooled again and filtered under suction. The filtrate is evaporated down, the residue is dissolved in sodium hydroxide solution and the solution is extracted with methylene chloride. After the solvent has been expelled, 2.8 g of the title compound remain.

NMR (CDCl₃): 7.35 s [1]; 7.15 s [1]; 4.38 t [2]; 3.30 s [2]; 2.85 t [2]; 2.19 s [6]; 1.70–1.90 m [2].

The following are prepared in a similar manner:

(b) 3-(4-Piperidinomethylpyrazol-1-yloxy)-propylamine

NMR (CDCl₃): 7.34 s [1]; 7.20 s [1]; 4.35 t [2]; 3.38 s [2]; 2.83 t [2]; 2.30–2.55 m [4]; 1.40–1.90 m [8].

(c) 4-(4-Piperidinomethylpyrazol-1-yloxy)-butylamine

NMR: see Example E(a).

(d) 5-(4-Piperidinomethylpyrazol-1-yloxy)-pentylamine

NMR (CDCl₃): 7.36 s [1]; 7.21 s [1]; 4.30 t [2]; 3.41 s [2]; 2.75 t [2]; 2.30–2.55 m [4]; 1.40–1.90 m [12].

Preparation of the compounds according to the invention:

EXAMPLE 1

2-[3-(4-Piperidinomethylpyrazol-1-yloxy)-propylamino]-5-(2-methylpyrid-5-ylmethyl)-1H-pyrimid-4-one 3.5 g of 3-(4-piperidinomethylpyrazol-1-yloxy)-propylamine and 3.6 g of 2-methylthio-5-(2-methylpyrid-5-ylmethyl)-1H-pyrimid-4-one in 30 ml of pyridine are refluxed for 30 hours. The pyridine is distilled off and the residue is then chromatographed over neutral Al₂O₃ (activity level III) using methylene chloride/3% strength methanol as the mobile phase. The oil obtained is reacted with tartaric acid in isopropanol to give an amorphous solid.

C₂₃H₃₁N₇O₂. 0.5 tartaric acid H₂O Calculated: C 51.1%, H 6.2%, N 14.4%. Found: C 51.3%, H 6.5%, N 14.4%.

NMR (DMSO-D₆): 8.31 s [1]; 8.00 s [1]; 7.45–7.55 m [2]; 7.20–7.37 m [1]; 7.12 d [1]; 4.29 t [2]; 4.15 (tartaric acid); 3.87 s [2]; 3.46 s [2]; 3.28–3.40 m [2]; 2.68–2.90 m [4]; 2.35 s [3]; 1.82 t [2]; 1.35–1.70 m [6].

EXAMPLE 2

1-Methyl-3-amino-5-[3-(4-piperidinomethylpyrazol-1-yloxy)propylamino]-1,2,4-triazole 5 g of 3-(4-piperidinomethylpyrazol-1-yloxy)-propylamine and 4.9 g of methyl N-cyano-1-methyl-2-(phenylmethylene)-hydrazinecarboximidothioate are combined, and heated at 70° C. for 1 hour. Thereafter, the reaction mixture is taken up with 40 ml of 1N hydrochloric acid, stirred for 1 hour at room temperature, rendered alkaline with sodium hydroxide solution and extracted with methylene chloride. The residue which remains after the solvent has been expelled is chromatographed over neutral Al₂O₃ (activity level III), using methylene chloride/3% strength methanol as the mobile phase. The oily title compound is reacted with tartaric acid in isopropanol to give an amorphous solid.

C₁₅H₂₆N₈O₄.0.5 tartaric acid.H₂O: Calculated: C 43.6%, H 6.4%, N 15.4%. Found: C 44.0%, H 6.7%, N 19.3;L %.

NMR (DMSO-D₆): 7.93 s [1]; 7.31 s [1]; 4.29 t [2]; 4.12 (tartaric acid; 3.85 s [2]; 3.22 s broad [2+3]; 2.70–2.88 m [4]; 1.82 t [2]; 1.35–1.70 m [6].

The following are prepared in a similar manner:

EXAMPLE 3

1-Methyl-3-amino-5-[4-(4-piperidinomethylpyrazol-1-yloxy)butylamino]-1,2,4-triazole C₁₆H₂₈N₈O.2 oxalic acid.H₂O: Calculated: C 43.9%, H 5.8%, N 20.5%. Found: C 43.7%, H 5.8%, N 19.7%.

NMR (DMSO-D$_6$): 7.91 s [1]; 7.38 s [1]; 4.27 t [2]; 4.03 s [2]; 3.28 s [3]; 3.15-3.25 m [2]; 2.65-2.90 m [4]; 1.55-1.75 m [10].

EXAMPLE 4

1-Methyl-3-amino-5-[5-(4-piperidinomethylpyrazol-1-yloxy)pentylamino]-1,2,4-triazole M.p.: 68°-71° C.

$C_{17}H_{30}N_8O.0.5$ $H_2O$: Calculated: C 55.7%, H 8.3%, N 30.6%. Found: C 55.5%, H 8.2%, N 30.4%.

NMR (DMSO-D$_6$): 7.65 s [1]; 7.16 s [1]; 4.22 t [2]; 3.38 s [2]; 3.26 s [3]; 3.09-3.18 m [2]; 2.19-2.37 m [4]; 1.28-1.70 m [12].

EXAMPLE 5

3-Amino-4-[4-(4-piperidinomethylpyrazol-1-yloxy)-butylamino]-cyclobutene-1,2-dione 2.5 g of 4-(4-piperidinomethylpyrazol-1-yloxy)-butylamine and 1.2 g of 3-amino-4-methoxycyclobutene-1,2-dione are introduced into 80 ml of methanol, and the mixture is stirred for 12 hours at 20° C. The solid formed is then filtered off under suction.

M.p.: 231° C.

$C_{17}H_{25}N_5O_3$: Calculated: C 58.7%, H 7.3%, N 20.2%. Found: C 58.3%, H 7.1%, N 20.2%.

NMR (DMSO-D$_6$): 7.62 s [1]; 7.14 s [1]; 4.27 t [2]; 3.38 s [2]; 3.10-3.15 m [2]; 2.20-2.40 m [4]; 1.29-1.80 m [10].

The following are prepared in a similar manner:

EXAMPLE 6

3-Methylamino-4-[4-(4-piperidinomethylpyrazol-1-yloxy)butylamino]-cyclobutene-1,2-dione M.p.: 178°-181° C. $C_{18}H_{27}N_5O_3$: Calculated: C 59.8%, H 7.5%, N 19.4%. Found: C 59.4%, H 7.5%, N 19.5%.

NMR (DMSO-D$_6$): 7.66 s [1]; 7.12 s [1]; 4.25 t [3]; 3.39 s [2]; 3.28 s [3]; 3.10-3.17 m [2]; 2.22-2.33 m [4]; 1.30-1.75 m [10].

EXAMPLE 7

4-Methylamino-3-[3-(4-piperidinomethylpyrazol-1-yloxy)propylamino]-1,2,5-thiadiazole 1-oxide 2.4 g of 4-methylamino-3-methoxy-1,2,5-thiadiazole 1-oxide and 3.5 g of 3-(4-piperidinomethylpyrazol-1-yloxy)propylamine are dissolved in 50 ml of methanol, and the solution is left to stand at room temperature for 12 hours. The solution is then evaporated down and the residue is chromatographed over neutral Al$_2$O$_3$ (activity level III), using methylene chloride/3% strength methanol as the mobile phase. 4 g of the title compound are obtained, the product being crystallized from ethyl acetate.

M.p.: 106° C.

$C_{15}H_{25}N_7O_2S$: Calculated: C 49.0%, H 6.5%, N 26.7%, S 8.7%. Found: C 48.4%, H 6.7%, N 26.6%, S 8.8%.

NMR (DMSO-D$_6$): 7.70 s [1]; 7.15 s [1]; 4.30 t [2]; 3.41-3.60 m [2]; 3.32 s [2]; 2.90 d [3]; 2.20-2.38 m [4]; 1.85-2.00 [2]; 1.28-1.50 m [6].

Examples 8 to 16 are prepared in a similar manner:

EXAMPLE 8

4-Amino-3-[3-(4-piperidinomethylpyrazol-1-yloxy)-propylamino]-1,2,5-thiadiazole 1-oxide $C_{14}H_{23}N_7O_2S.0.5$ $H_2O$: Calculated: C 46.4%, H 6.6%, N 27.1%. Found: C 46.0%, H 6.4%, N 27.0%.

NMR (DMSO-D$_6$): 7.76 s [1]; 7.18 s [1]; 4.32 t [2]; 2.44-3.56 m [2]; 3.35 s [2]; 2.28-2.45 m [49 ; 1.86-2.00 m [2]; 1.32-1.56 m [6].

EXAMPLE 9

4-Amino-3-[3-(4-N,N-dimethylaminomethylpyrazol-1-yloxy)propylamino]-1,2,5-thiadiazole 1-oxide $C_{11}H_{19}N_7SO_2.0.7$ $H_2O$: Calculated: C 40.6%, H 6.3%, N 30.1%, S 9.8%. Found: C 41.4%, H 6.3%, N 29.8%, S 9.6%.

NMR (DMSO-D$_6$): 7.74 s [1]; 7.17 s [1]; 4.34 t [2]; 3.45-3.56 m [2]; 3.28 s [2]; 2.12 s [6]; 1.90-2.00 m [2].

EXAMPLE 10

4-Amino-3-[4-(4-piperidinomethylpyrazol-1-yloxy)-butylamino]-1,2,5-thiadiazole 1-oxide M.p.: 135°-138° C.

NMR (DMSO-D$_6$): 7.65 s [1]; 7.15 s [1]; 4.23 t [2]; 3.35-3.50 m [2]; 3.30 s [2]; 2.20-2.40 m [4]; 1.60-1.80 m [4]; 1.25-1.55 m [6].

EXAMPLE 11

4-Amino-3-[5-(4-piperidinomethylpyrazol-1-yloxy)-pentylamino]-1,2,5-thiadiazole 1-oxide M.p.: 125°-127° C.

$C_{16}H_{27}N_7O_2S$: Calculated: C 50.3%, H 7.1%, N 25.7%, S 8.4%. Found: C 49.8%, H 7.2%, N 25.3%, S 8.3%.

NMR (DMSO-D$_6$): 7.65 s [1]; 7.15 s [1]; 4.25 t [2]; 3.25-3.45 m [4]; 2.20-2.40 m [4]; 1.55-1.70 m [4]; 1.30-1.50 m [8].

EXAMPLE 12

4-Methylamino-3-[4-(4-piperidinomethylpyrazol-1-yloxy)butylamino]-1,2,5-thiadiazole 1-oxide $C_{16}H_{27}N_7O_2S$: Calculated: C 50.3%, H 7.1%, N 25.7%, S 8.4%. Found: C 49.7%, H 7.3%, N 25.4%, S 8.4%.

NMR (DMSO-D$_6$): 7.65 s [1]; 7.15 s [1]; 4.25 t [2]; 3.35-3.50 m [2]; 3.25 s [2]; 2.90 d [3]; 2.20-2.40 m [4]; 1.60-1.80 m [4]; 1.25-1.55 m [6].

EXAMPLE 13

4-Amino-3-[4-(4-morpholinomethylpyrazol-1-yloxy)-butylamino]-1,2,5-thiadiazole 1-oxide M.p.: 115° C.

$C_{14}H_{23}N_7SO_3$: Calculated: C 45.5%, H 6.3%, N 26.5%, S 8.7%. Found: C 45.2%, H 6.3%, N 26.2%, S 8.6%.

NMR (DMSO-D$_6$): 7.65 s [1]; 7.15 s [1]; 4.25 t [2]; 3.45-3.60 m [4]; 3.25-3.40 m [4]; 2.20-2.40 m [4]; 1.60-1.80 m [4].

EXAMPLE 14

4-Amino-3-[4-(4-pyrrolidinomethylpyrazol-1-yloxy)-butylamino]-1,2,5-thiadiazole 1-oxide M.p.: 100° C. (decomposition).

$C_{14}H_{23}N_7SO_2$: Calculated: C 47.6%, H 6.6%, N 27.7%, S 9.1%. Found: C 47.2%, H 6.6%, N 27.2%, S 8.7%.

NMR (DMSO-D$_6$): 7.65 s [1]; 7.15 s [1]; 4.26 t [2]; 3.25-3.60 m [4]; 2.35-2.50 m [4]; 1.50-1.80 m [8].

EXAMPLE 15

4-Amino-3-[4-(4-N-methyl-N-benzylaminomethyl-pyrazol-1-yloxy)-butylamino]-1,2,5-thiadiazole 1-oxide M.p.: 116° C.

$C_{18}H_{25}N_7SO_2$: Calculated: C 53.6%, H 6.8%, N 24.3%, S 7.9%. Found: C 53.1%, H 6.4%, N 23.9%, S 7.8%.

NMR (DMSO-$D_6$): 7.75 s [1]; 7.22–7.38 m [5]; 7.20 s [1]; 4.25 t [2]; 3.30–3.45 m [6]; 2.05 s [3]; 1.60–1.80 m [4].

EXAMPLE 16

4-Amino-3-[4-(4-N,N-di-n-butylaminomethylpyrazol-1-yloxy)butylamino]-1,2,5-thiadiazole 1-oxide M.p.: 115° C.

$C_{18}H_{33}N_7O_2$: Calculated: C 52.5%, H 8.1%, N 23.8%, S 7.8%. Found: C 51.9%, H 8.1%, N 23.3%, S 7.6%.

EXAMPLE 17

N-Methyl-N'-[3-(4-piperidinomethylpyrazol-1-yloxy)-propylamino]-cyanoguanidine 4.3 g of 3-(4-piperidinomethylpyrazol-1-yloxy)-propylamine and 2.7 g of dimethyl cyanodithioimidocarbonate are dissolved in 50 ml of methanol, and the solution is left to stand for 12 hours at room temperature. Thereafter, 12 ml of a 16 percent strength methanolic methylamine solution are added and the mixture is kept at 50° C. for 24 hours. The solvent is evaporated off and the residue is then chromatographed over neutral $Al_2O_3$ (activity level III), using methylene chloride as the mobile phase. 4 g of the title compound are obtained.

$C_{15}H_{25}N_7O.0.5 H_2O$: Calculated: C 54.1%, H 8.0%, N 29.5%. Found: C 54.1%, H 7.9%, N 29.4%.

NMR (DMSO-$D_6$): 7.68 s [1]; 7.16 s [1]; 4.24 t [2]; 3.24–3.38 m [2]; 3.29 s [2]; 2.65–2.76 m [2]; 2.22–2.40 m [4]; 1.75–1.92 m [2]; 1.30–1.56 m [6].

EXAMPLE 18

1-Methylamino-1-[3-(4-N,N-dimethylaminomethyl-pyrazol-1-yloxy)-propylamino]-2-nitroethylene 3.1 g of 3-(4-N,N-dimethylaminomethylpyrazol-t-yloxy)-propylamine and 2.3 g of 1-methylthio-1-methylamino-2-nitroethylene are dissolved in 30 ml of methanol, and the solution is left to stand at room temperature for 12 hours. Thereafter, the solution is evaporated down and the residue is chromatographed over neutral alumina (activity level III), using methylene chloride/2% strength methanol as the mobile phase. 1.4 g of the title compound are obtained as a colorless oil.

$C_{12}H_{22}N_6O_3.0.75$ methanol.0.5 $H_2O$: Calculated: C 45.8%, H 7.8%, N 25.6%. Found: C 45.9%, H 7.5%, N 25.7%.

NMR (DMSO-$D_6$): 7.75 s [1]; 7.20 s [1]; 6.45–6.65 m [1]; 4.32 t [2]; 3.45–3.55 m [2]; 3.28 s [2]; 2.72–2.95 m [3]; 2.12 s [6]; 1.84–1.58 m [2].

The following are obtained in a similar manner:

EXAMPLE 19

1-Methylamino-1-[3-(4-piperidinomethylpyrazol-1-yloxy)propylamino]-2-nitroethylene $C_{15}H_{26}N_6O_3.0.5 H_2O.0.5$ methanol: Calculated: C 51.2%, H 8.0%, N 23.1%. Found: C 51.3%, H 7.8%, N 23.4%.

NMR (DMSO-$D_6$): 7.72 s [1]; 7.16 s [1]; 6.52 s broad [1]; 4.30 t [2]; 3.46–3.60 m [2]; 3.29 s [2]; 2.70–2.95 m [3]; 2.24–2.38 m [4]; 1.82–1.98 m [2]; 1.30–1.55 m [6].

EXAMPLE 20

1-Methylamino-1-[4-(4-piperidinomethylpyrazol-1-yloxy)butylamino]-2-nitroethylene $C_{16}H_{28}N_6O_3$.tartaric acid.isopropanol.$H_2O$ Calculated: C 47.5%, H 7.6%, N 14.5%. Found: C 47.9%, H 7.7%, N 14.4%.

NMR (DMSO-$D_6$): 7.91 s [1]; 7.37 s [1]; 6.50 s [1]; 4.32 t [2]; 4.15 (tartaric acid); 3.90 s [2]; 3.10–3.30 m [2]; 2.65–2.95 m [7]; 1.40–1.75 m [10].

EXAMPLE 21

3-[4-(4-Piperidinomethylpyrazol-1-yloxy)-butylamino]-benzoisothiazole 1,1-dioxide 3.5 g of 4-(4-piperidinomethylpyrazol-1-yloxy)-butylamine and 1.4 g of triethylamine are dissolved in 50 ml of methylene chloride. A solution of 2.8 g of 3-chlorobenzoisothiazole 1,1-dioxide in 15 ml of methylene chloride is then added dropwise. After standing for 3 hours at room temperature, the reaction mixture is washed with water, the organic phase is evaporated down and the residue is chromatographed over neutral $Al_2O_3$ (activity level III), using methylene chloride as the mobile phase. 1.7 g of the title compound are obtained, the product being crystallized from ether.

M.p.: 86°–89° C.

$C_{20}H_{27}N_5SO_3.0.5 H_2O$: Calculated: C 56.2%, H 6.6%, N 16.4%, S 7.5%. Found: C 56.5%, H 6.6%, N 16.6%, S 7.6%.

NMR (DMSO-$D_6$): 8.15–8.25 m [1]; 7.90–8.00 m [1]; 7.75–7.85 m [2]; 7.65 s [1]; 7.15 s [1]; 4.25 t [2]; 3.50 m [2]; 3.22 s [2]; 2.10–2.35 m [4]; 1.60–1.90 m [4]; 1.20–1.55 m [6].

EXAMPLE 22

4-Amino-3-[4-(4-piperidinomethylpyrazol-1-yloxy)-butylamino]-1,2,5-thiadiazole 2.7 g of 4-amino-3-[4-(4-piperidinomethylpyrazol-1-yloxy)-butylamino]-thiadiazole 1-oxide are dissolved in 70 ml of methanol, and 6 ml of concentrated hydrochloric acid are added. The mixture is left to stand for 6 hours at 25° C. and then evaporated down under reduced pressure, the residue is taken up in 80 ml of methylene chloride, and 9 ml of triethylamine are added. 2.4 g of N,N-thiobisphthalimide are then added. After a further 3 hours at 25° C., the mixture is washed with 50 ml of 2N potassium hydroxide solution, and the organic phase is evaporated down. The residue is chromatographed over neutral $Al_2O_3$ (activity level III), using methylene chloride/2% strength methanol as the mobile phase. 1.0 g of the desired product are obtained, and the product is converted to an amorphous salt with tartaric acid in methanol.

NMR (DMSO-$D_6$): 7.85 s [1]; 7.30 s [1]; 4.25 t [2]; 4.10 (tartaric acid); 3.80 s [2]; 3.25–3.35 m [2]; 2.70–2.90 m [4]; 1.40–1.75 m [10].

We claim:

1. A 1,4-disubstituted pyrazole derivative of the formula I

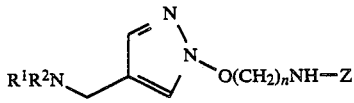

where $R^1$ and $R^2$ independently of one another are each hydrogen, lower alkyl or benzyl, or $R^1$ and $R^2$, together with the nitrogen atom to which they are bonded, may be a pyrrolidino, piperidino or morpholino radical, n is an integer from 2 to 5, and Z is a radical of the formula $QNR^1R^2$ where $R^1$ and $R^2$ have the same meanings as above, Q is

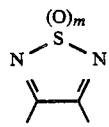

and m may be 0 or 1, and its pharmaceutically tolerated salts.

2. The pyrazole derivative of claim 1 which is 4-Amino-3-[4-(4-piperidinomethylpyrazol-1-yloxy)-butylamino]-1,2,5-thiadiazole 1-oxide.

3. The pyrazole derivative of claim 1 which is 4-Methylamino-3-[4-(4-piperidinomethylpyrazol-1-yloxy)-butylamino]-1,2,5-thiadiazole 1-oxide.

4. The pyrazole derivative of claim 1 which is 4-Amino-3-[4-(4-pyrrolidinomethylpyrazol-1-yloxy)-butylamino]-1,2,5-thiadiazole 1-oxide.

5. The pyrazole derivative of claim 1 which is 4-Amino-3-[4-(4-piperidinomethylpyrazol-1-yloxy)-butylamino]-1,2,5-thiadiazole.

6. A composition for the treatment of disorders associated with a pathologically increased secretion of gastric acid, which contains, in addition to conventional pharmaceutical auxiliaries, an effective amount of a compound of the formula I as claimed in claim 1 or of one of its physiologically tolerated salts as an active compound.

7. A method of treating a patient suffering from a pathologically increased secretion of gastric acid which comprises: administering to said patient an amount of pyrazole derivative as defined in claim 1 effect to inhibit the secretion of gastric acid.

* * * * *